(12) United States Patent
Jones et al.

(10) Patent No.: US 7,141,067 B2
(45) Date of Patent: Nov. 28, 2006

(54) INTERCALARY IMPLANT

(75) Inventors: Michael C. Jones, North Webster, IN (US); Natalie S. Heck, Leesburg, IN (US)

(73) Assignee: Depuy Products, Inc., Warsaw, IN (US)

( * ) Notice: Subject to any disclaimer, the term of this patent is extended or adjusted under 35 U.S.C. 154(b) by 209 days.

(21) Appl. No.: 10/403,357

(22) Filed: Mar. 31, 2003

(65) Prior Publication Data
US 2004/0193267 A1    Sep. 30, 2004

(51) Int. Cl.
*A61F 2/28*    (2006.01)
*A61B 17/56*    (2006.01)

(52) U.S. Cl. .................. 623/16.11; 606/62; 606/63

(58) Field of Classification Search .............. 623/16.11, 623/18.11, 23.44, 23.47; 606/60, 64, 62, 606/63, 68
See application file for complete search history.

(56) References Cited

U.S. PATENT DOCUMENTS

| | | | |
|---|---|---|---|
| 4,011,602 A | 3/1977 | Rybicki | |
| 4,016,874 A * | 4/1977 | Maffei et al. | .................. 606/62 |
| 4,384,373 A | 5/1983 | Sivash | |
| 4,467,794 A * | 8/1984 | Maffei et al. | .................. 606/62 |
| 4,502,160 A | 3/1985 | Moore et al. | |
| 4,634,444 A | 1/1987 | Noiles | |
| 4,655,462 A | 4/1987 | Balsells | |
| 4,676,797 A | 6/1987 | Anapliotis et al. | |
| 4,787,907 A * | 11/1988 | Carignan | .................. 623/23.44 |
| 4,826,144 A | 5/1989 | Balsells | |
| 4,830,344 A | 5/1989 | Balsells | |
| 4,876,781 A | 10/1989 | Balsells | |
| 4,888,021 A | 12/1989 | Forte | |
| 4,915,366 A | 4/1990 | Balsells | |
| 4,934,666 A | 6/1990 | Balsells | |
| 4,938,768 A | 7/1990 | Wu | |
| 5,011,496 A | 4/1991 | Forte | |
| 5,072,070 A | 12/1991 | Balsells | |
| 5,079,388 A | 1/1992 | Balsells | |
| 5,082,390 A | 1/1992 | Balsells | |

(Continued)

FOREIGN PATENT DOCUMENTS

DE    3535158 A    4/1987

(Continued)

OTHER PUBLICATIONS

Centerpulse Orthopedics, Inc. web site announcement: *Centerpulse Orthopedics Announces Launch of Implant System for Revision and Trauma Patients*: http://www.centerpulseorthopedics.com/us/products/news/most options launch 12 09. (4 pages); Dec. 9, 2002.

(Continued)

*Primary Examiner*—Pedro Philogene

(57) ABSTRACT

An intercalary implant has two stem members and a collar. One stem member includes a stem portion to be received in the intramedullary canal of a native end portion of a long bone and a threaded male portion to be outside of the intramedullary canal. The second stem member also includes a stem portion to be received in the intramedullary canal of the opposite native end portion of the long bone. The second stem member has a spacer portion and a shoulder to be outside of the intramedullary canal. The collar has an annular base portion with an opening and a cylindrical female threaded portion. When assembled, collar connects the first and second stem members and the implant spans a gap in the shaft of the long bone. The parts can be assembled without distracting the native end bone portions in the proximal-distal direction to prevent damage to soft tissue around the native end bone portions.

16 Claims, 7 Drawing Sheets

U.S. PATENT DOCUMENTS

| | | | |
|---|---|---|---|
| 5,100,407 A | 3/1992 | Conrad | |
| 5,108,078 A | 4/1992 | Balsells | |
| 5,117,066 A | 5/1992 | Balsells | |
| 5,139,276 A | 8/1992 | Balsells | |
| 5,314,479 A | 5/1994 | Rockwood | |
| 5,334,184 A * | 8/1994 | Bimman | 606/63 |
| 5,352,227 A * | 10/1994 | O'Hara | 606/63 |
| 5,358,524 A | 10/1994 | Richelsoph | |
| 5,411,348 A | 5/1995 | Balsells | |
| 6,197,065 B1 | 3/2001 | Martin et al. | |
| 6,290,725 B1 | 9/2001 | Weiss | |
| 6,364,909 B1 | 4/2002 | McGee | |
| 6,447,549 B1 | 9/2002 | Taft | |
| 6,454,810 B1 | 9/2002 | Lob | |
| 6,613,092 B1 | 9/2003 | Kana et al. | |
| 6,712,855 B1 | 3/2004 | Martin et al. | |
| 6,712,858 B1 | 3/2004 | Grundei et al. | |
| 2001/0041941 A1 | 11/2001 | Boyer, II et al. | |
| 2003/0149486 A1 | 8/2003 | Huebner | |
| 2003/0204262 A1 | 10/2003 | Ferguson | |

FOREIGN PATENT DOCUMENTS

| | | |
|---|---|---|
| DE | 3903438 A | 8/1990 |
| DE | 19633865 A | 2/1998 |
| DE | 19722389 A | 12/1998 |
| EP | 0 212 192 A | 3/1987 |
| EP | 1234557 A | 8/2002 |
| EP | 1358860 A | 11/2003 |
| FR | 2633509 A | 1/1990 |
| WO | WO 02/05732 A | 1/2002 |

OTHER PUBLICATIONS

Centerpulse Orthopedics, Inc. web site page: MOST Options™; *Modular Knee and Hip Otpions for Severe Bone Loss and Trauma*; http://www.centerpulseorthopedics.com/most options/knee/index. (2 pages).

Wright Medical Technology, Inc.: Guardian™ Limb Salvage System: Surgical Technique brochure: *Total Femoral Replacement*. 2001, Wright Medical Technology, Inc. (19 pages).

Wright Medical Technology, Inc.,: Guardian™ Limb Salvage System: Surgical Technique brochure: *Distal Femoral Replacement* 2001, Wright Medical Technology, Inc. (19 pages).

Wright Medical Technology, Inc., Guardian™ Limb Salvage System: Surgical Technique brochure: *Proximal Femoral Replacement*. 2001, Wright Medical Technology, Inc. (11 pages).

Biomet®, Inc, website: *Finn® Salvage/oncology System*; http://www.biomet.com/knees/finn.cfm 2001, 2002. (Form No. Y-BMT-698/123100/M) (2 pages).

Howmedica Osteonics Corp. web site: Product Overview: *Modular-Replacement System*: http://www.howost.com/kneesystems/mrs/text.php: http://www.howost.com/kneesystems/mrs/overview.htm; http://www.howost.com/kneewsystem/mrs/proxfemur.htm: http://www.howost.com/kneesystems/mrs/distalfemur.htm; http://www.howost.com/kneesystems/mrs/totalfemurr.htm: http://www.howost.com/kneesystems/mrs/proxtibiar.htm; http://www.howost.com/kneesystems/mrs/shoulderrhtm. 1997, Howmedica Osteonics Corp. (7 pages).

Biomet®, Inc. *Knee System Modularity and Surgical Latitude* brochure. 1995. (Form No. &-BMT-382/021095/H) (22 pages).

Biomet®, Inc. *Proximal Humeral Replacement™ System* brochure 1996. (Form No. Y-BMT-466/043096/H) (2 pages).

Biomet®, Inc. *Finn™ Knee System Product Release Overview* brochure, including pp. 1-30.

Biomet®, Inc. *The Finn Knee: Rotating Hinge Replacement of the Knee Preliminary Report of New Design* document, pp. 413-416.

Howmedica Osteonics Corp. Modular Replacement System: *A Simple, Comprehensive, Modular System for Radical Bone Resections of Proximal Femur, Distal Femur, Total Femur, Proximal Tibia, Proximal Humerus* brochure. 1997 Howmedica, Inc. (7100-0-001-0 5M Sep. 1997 5807 TG/HAR). (6 pages).

Stryker Howmedica Osteonics Corp: *Modular Rotating Hinge Knee System* brochure. 2000 Stryker COrporation (6481-2-085 LI Jun. 2000). (4 pages).

Howmedica International: *Howmedica Modular Resection System* brochure (XXK/01/0391/4E). (12 pages).

Sulzer Medica: *Sulzer™ Orthopedics MOST™ System* brochure (1000-01-607) (Oct. 1997 1.5M 1997 Sulzer Orthopedics, Inc. (2 pages).

Wright Medical Technology, Inc.: Segmental Oncology System—*The S.O.S. Proximal Femur* brochure (4 pages).

Wright Medical Technology, Inc.: Segmental Orthopedic System—*The Salvage Solution—The S.O.S. Proximal Femur* brochure (7 pages).

Balseal Engineering, Canted Coil Springs web page: Aug. 21, 2002.

Stryker Howmedica Osteonics: *Modular Replacement System: Distal Femoral Resection for Large Segmental Replacements*—Surgical Technique Brochure.

European Search Report dated Dec. 5, 2005, for corresponding EP application 04251869.6.

International Search Report dated May 11, 2006, regarding PCT Application No. PCT/US05/45197.

* cited by examiner

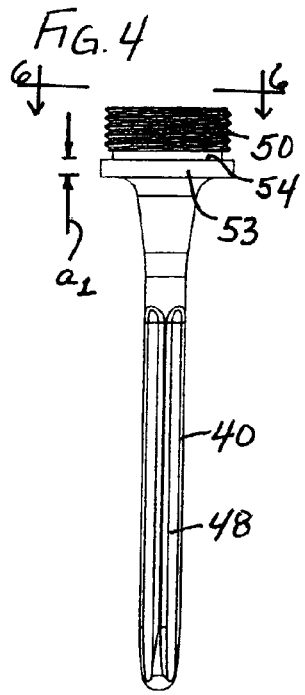
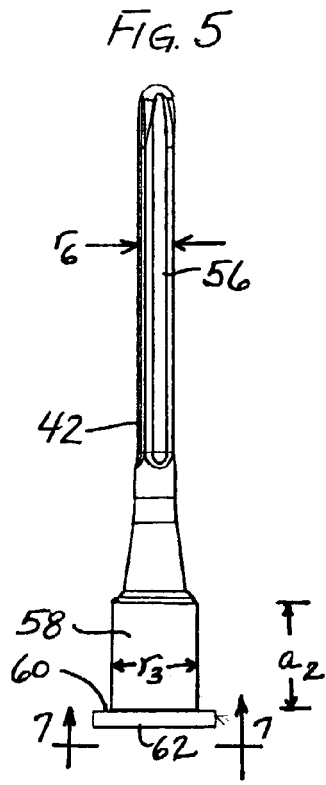
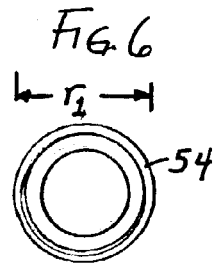
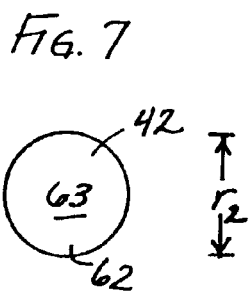
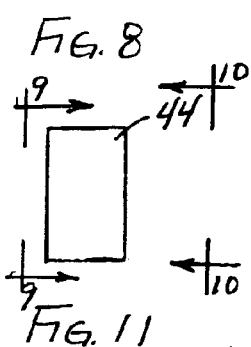
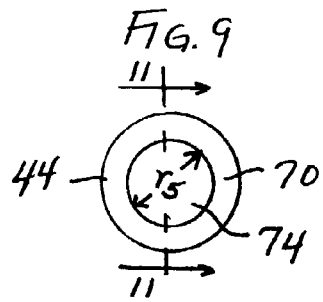
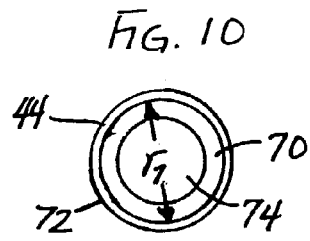
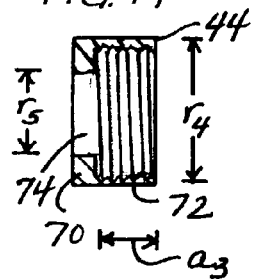
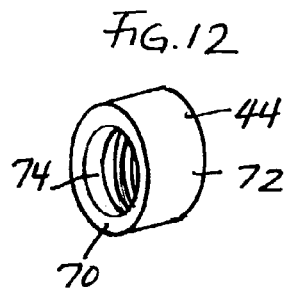

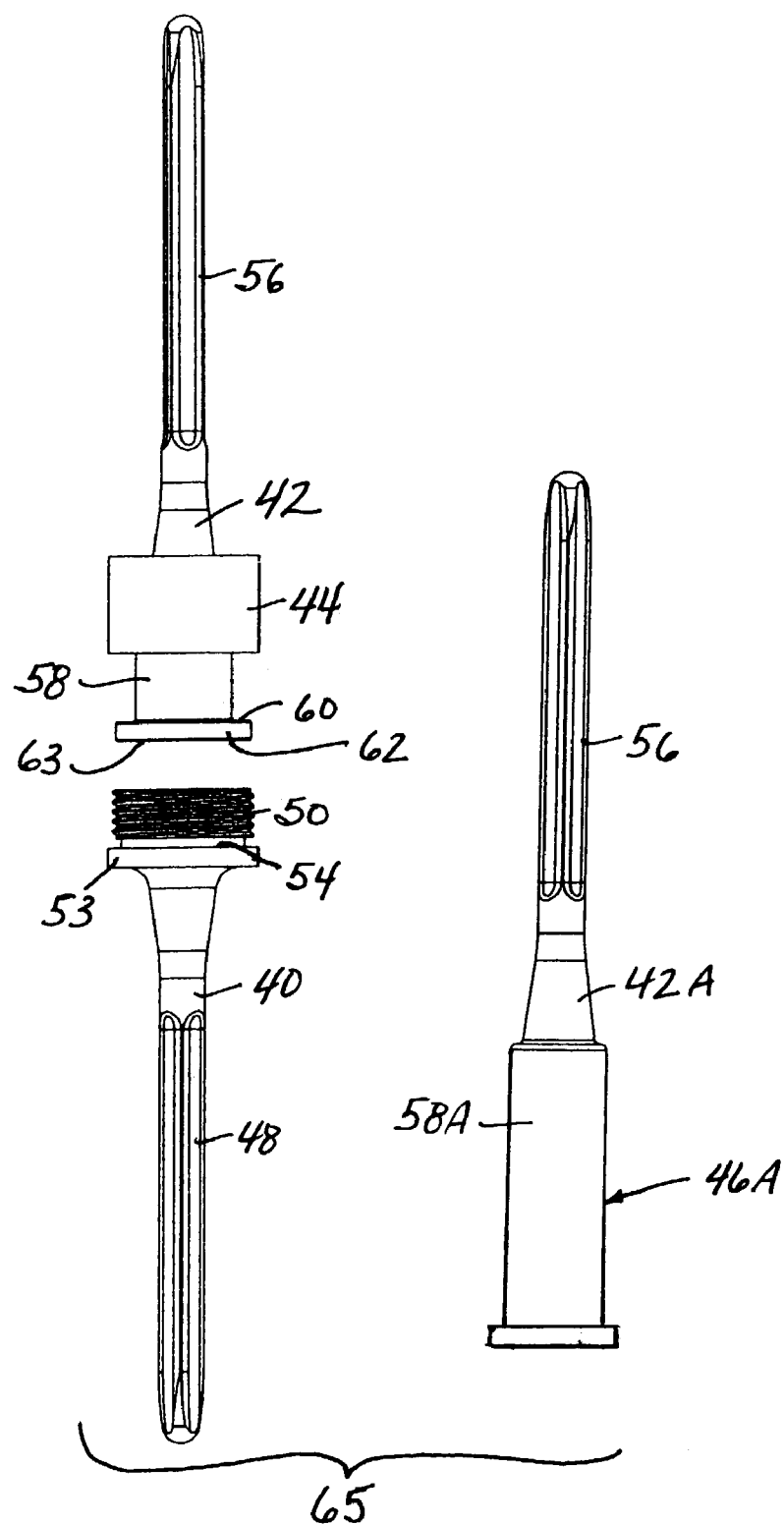

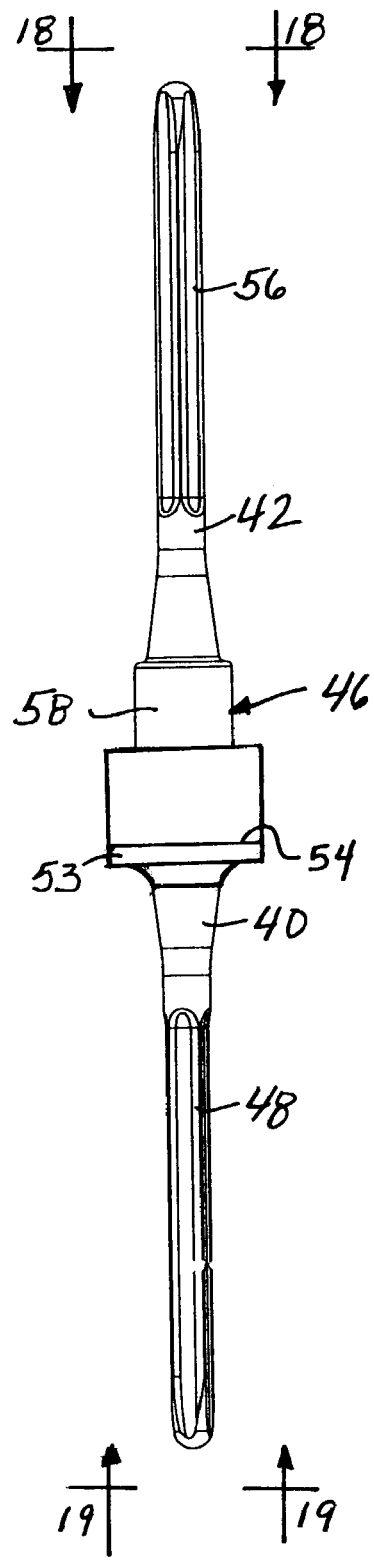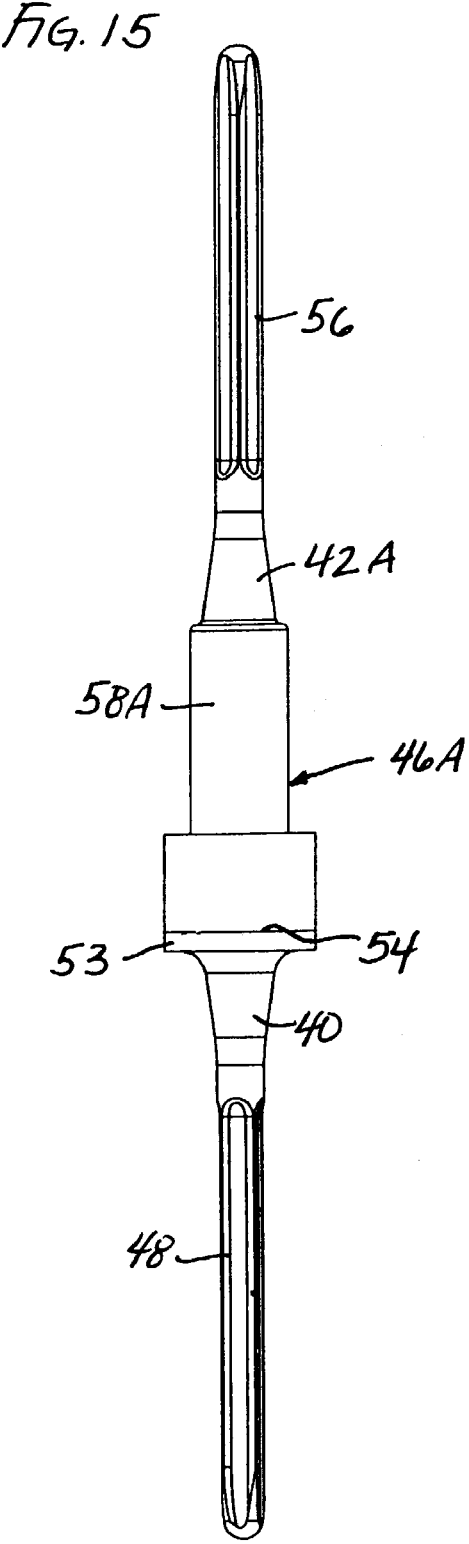

INTERCALARY IMPLANT

FIELD OF THE INVENTION

The present invention relates to prosthetic systems for replacement of parts of bones, and more particularly to prosthetic systems for replacement of mid-shaft parts of long bones.

BACKGROUND OF THE INVENTION

Severe trauma and disease can lead to significant amounts of bone loss. In some instances, it is necessary to excise intercalary bone from a long bone, that is, part of the diaphysis or bone shaft between the ends of the long bone, but it is not necessary to excise the ends of the long bone. Thus, for example, a portion of the shaft of the humerus may need to be excised to remove a malignancy, while the ends of the humerus defining parts of the shoulder and elbow joint may be healthy. Similarly, it may be necessary to excise part of the shaft of the tibia or femur while the ends of these bones are healthy. Rather than remove the healthy ends of the bone, it may be desirable to leave the healthy portions of the bone in place and remove the damaged or diseased bone. In these circumstances, the empty span between the ends of the bone must be replaced with some type of mid-shaft prosthesis that spans the distance between the native bone ends. The mid-shaft prosthesis can include stems that fit into the intramedullary canals of the native bone ends and a body that extends between these stems. However, it may be difficult to implant such a mid-shaft prosthesis. Implantation can require that the native bone ends be distracted proximally and distally in order to fit the mid-shaft prosthesis into position. Since the native bone ends are surrounded by and connected to soft tissue, distraction of the native bone ends can damage the soft tissue and the connections between the soft tissue and the native bone ends.

Moreover, different bones undergo different types of stress in use. For example, the femur and tibia will tend to be subjected to compressive forces, while the humerus, radius and ulna will tend to be subjected to tension.

SUMMARY OF THE INVENTION

The present invention addresses the need for intercalary prosthetics that can be used to replace portions of the diaphyseal parts of the long bone that have been removed or excised. The present invention addresses this need while also addressing the need for such prosthetics that can be implanted and affixed to the remaining parts of the native bone while minimizing damage to soft tissue at the ends of the native bone.

In one aspect, the present invention provides an intercalary implant for use in replacing a missing portion of the shaft of a long bone, wherein the long bone includes native proximal and distal portions having intramedullary canals. The implant comprises a first stem member, a second stem member and a collar. The first stem member includes a stem portion to be received in the intramedullary canal of one of the native portions of the long bone and a threaded male portion to be positioned outside of the intramedullary canal. The second stem member includes a stem portion to be received in the intramedullary canal of the other of the native portions of the long bone. The second stem member further includes a spacer portion to be positioned outside of the intramedullary canal and a shoulder to be positioned outside of the intramedullary canal. The spacer portion is between the stem portion and the shoulder. The collar includes an annular base portion with an opening and a cylindrical portion open at one end. The cylindrical portion has a threaded interior surface to receive and mate with the threaded male portion of the first stem member. The collar receives part of the second stem member through the opening in the base portion of the collar, and the collar is movable in a proximal-distal direction along at least part of the length of the spacer portion of the second stem member between an extended position and a retracted position. In the extended position the annular base portion of the collar is spaced from the stem portion of the second stem member and abuts the shoulder of the second stem member and the cylindrical portion of the collar extends over and beyond the shoulder of the second stem member. In the retracted position the collar is positioned so that at least part of the shoulder is exposed. The shoulder and the opening of the annular base portion of the collar are sized and shaped so that when the collar is threaded onto the threaded male portion of the first stem member the position of the first stem member is fixed with respect to the position of the second stem member.

In another aspect, the present invention provides a surgical kit for use in treating a long bone of a patient wherein a portion of the shaft of the long bone is missing or resected and native proximal and distal portions of the long bone remain. The kit comprises a first stem member, a second stem member and a collar. The first stem member includes a stem portion and a threaded male portion. The second stem member has an overall axial dimension and includes a stem portion, a spacer portion having an axial dimension and a radial dimension, and a shoulder having an axial dimension and a radial dimension. The spacer portion is between the stem portion and the shoulder. The radial dimension of the shoulder is greater than the radial dimension of the spacer portion. The collar member includes an annular base portion with an opening and a cylindrical portion open at one end. The collar member has a threaded interior surface to receive and mate with the threaded male portion of the first stem member. The cylindrical portion has an interior radial dimension and an axial dimension. The annular base portion has a radial dimension and the opening of the annular base portion has a radial dimension. The radial dimension of the shoulder of the second stem member is greater than the radial dimension of the opening in the annular base portion of the collar. The interior radial dimension of the cylindrical portion of the collar is greater than the radial dimension of the spacer of the second stem member and the radial dimension of the shoulder of the second stem member. The axial dimension of the cylindrical portion of the collar is greater than the axial dimension of the shoulder of the second stem member.

In another aspect, the present invention provides a method of surgically replacing a missing part of the shaft of a long bone. The method comprises preparing the long bone so that proximal and distal portions of the long bone remain. The proximal and distal portions of the long bone each having an intramedullary canal. An intercalary implant is provided. The intercalary implant has a first stem member, a second stem member and a collar. The first stem member includes a stem portion and a male threaded portion. The second stem member includes a stem portion, a spacer and a shoulder. The collar includes a female threaded portion. The stem portion of one of the stem members is implanted in the intramedullary canal of the proximal portion of the long bone. The stem portion of the other of the stem members is implanted in the intramedullary canal of the distal portion of the long bone. The male portion of the first stem member is positioned against the shoulder of the second stem member without distracting the proximal and distal parts of the bone in the proximal-distal direction. The collar is threaded onto the threaded male portion of the second stem member without distracting the proximal and distal parts of the bone in the proximal-distal direction to assemble the intercalary implant.

In another aspect, the present invention provides, in combination, a proximal portion of a long bone, a distal portion of the long bone and an intercalary implant. The proximal portion has an intramedullary canal and a resected end surface. The distal portion has an intramedullary canal and a resected end surface. The two resected end surfaces are spaced from each other. The intercalary implant comprises a first stem member, a second stem member and a collar. The first stem member has a stem portion received in the intramedullary canal of one of the portions of the long bone. The second stem member has a stem portion received in the intramedullary canal of the other portion of the long bone. One of the stem members also has a male threaded member. The collar has a female threaded portion engaging the male threaded member. The other stem member has a spacer and a shoulder connected to its stem portion. At least a portion of the collar bears against a portion of the shoulder. The distance between the resected end surfaces of the bone portions is fixed by the intercalary implant.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 4 is an elevation of an exemplary first stem member component of the intercalary implant of the present invention;

FIG. 5 is an elevation of an exemplary second stem member component of the intercalary implant of the present invention;

FIG. 6 is an end view of the stem member component of FIG. 4, taken from the perspective of line 6—6 of FIG. 4;

FIG. 7 is an end view of the stem member component of FIG. 5, taken from the perspective of line 7—7 of FIG. 5;

FIG. 8 is an elevation of an exemplary collar component of the intercalary implant of the present invention;

FIG. 9 is an end view of the collar component of FIG. 8, taken from the perspective of line 9—9 of FIG. 8;

FIG. 10 is an opposite end view of the collar component of FIGS. 8–9, taken from the perspective of line 10—10 of FIG. 8;

FIG. 11 is a cross-section of the collar component of FIGS. 8–10, taken along line 11—11 of FIG. 9;

FIG. 12 is a perspective view of the collar component of FIGS. 8–11;

FIG. 13 is an elevation of a kit including first, second and third stem members and a collar component;

FIG. 14 is an elevation of an exemplary embodiment of an intercalary implant assembled from the components of FIGS. 4–12;

FIG. 15 is an elevation of an exemplary embodiment of an assembled intercalary implant for use in spanning a longer gap in a bone;

DETAILED DESCRIPTION

Figure 1:
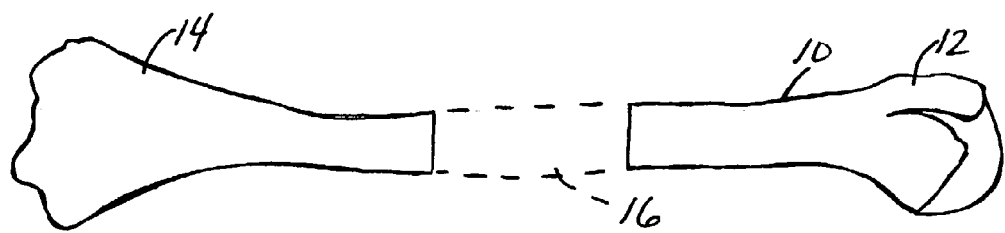
FIG. 1 is a top plan or anterior view of a humerus, showing the native proximal and distal ends of the humerus and showing an excised intercalary segment of the diaphysis of the humerus in phantom between the native ends of the humerus.

FIG. 1 illustrates a long bone, and in particular, a humerus 10 with proximal and distal ends 12, 14. The proximal end 12 of the humerus 10 comprises the head and adjacent bone tissue; the distal end 14 of the humerus 10 comprises the trochlea and adjacent bone tissue. FIG. 1 also illustrates in phantom the intercalary segment 16 of diaphyseal bone that has been removed, due to, for example, disease or severe trauma. Although the present invention is illustrated in use with the humerus, it should be understood that the invention is not so limited; the invention could be used in any other long bone, such as the tibia or femur, where a portion of the shaft has been removed or is missing.

Figure 2:
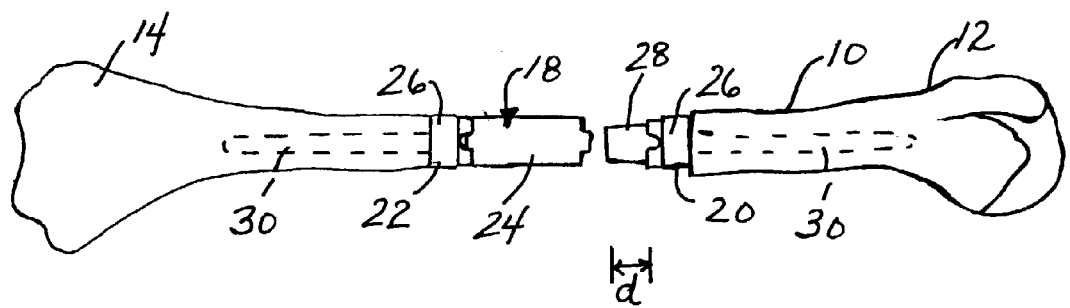
FIG. 2 is a top plan or anterior view of the humerus of FIG. 1, shown with one type of intercalary prosthesis prior to assembly of all the parts of the intercalary prosthesis.
Figure 3:
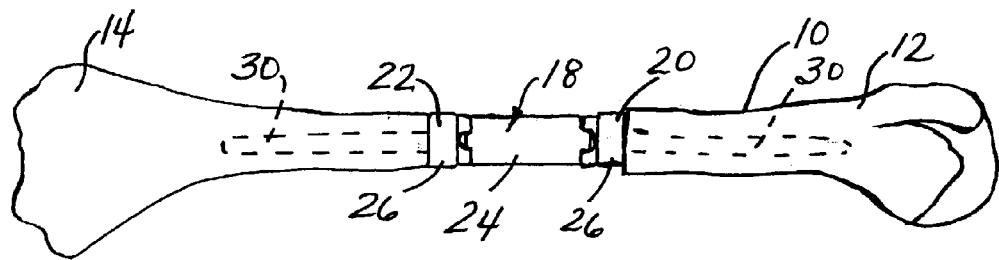
FIG. 3 is a top plan or anterior view of the humerus of FIGS. 1–2, shown with all parts of the intercalary prosthesis assembled together.

FIG. 2 illustrates the humerus 10 of FIG. 1 in an intra-operative state, with a modular mid-shaft prosthesis 18. FIG. 3 illustrates the humerus 10 of FIGS. 1–2 at the end of the surgical procedure. The mid-shaft prosthesis 18 of FIG. 2 is like that disclosed in U.S. patent application Ser. No. 10/135,791 filed on Apr. 30, 2002 and entitled "Modular Limb Preservation System," and is shown at FIGS. 5 and 9 of that patent application. That patent application is incorporated by reference herein in its entirety.

The mid-shaft prosthesis 18 illustrated in FIGS. 2–3 comprises a proximal stem component 20, a distal stem component 22 and a spacer component 24. Each of the stem components 20, 22 includes a head portion 26 from which extends a male connection element Morse taper post 28. The head portion 26 also includes a pair of notches that receive tabs on the spacer component 24. Each of the stem components 20, 22 also includes a stem portion 30 that is shaped to be received in the intramedullary canal of the bone.

As shown in FIG. 2, to implant the mid-shaft prosthesis 18 in the bone 10, the two stem components 20, 22 may be implanted in the intramedullary canals of the two spaced ends 12, 14 of the bone 10. The spacer component 24 can be connected to one of the stem portions 20, 22 before the stem portion is implanted, or could also be connected after the stem portion is implanted. To complete the assembly, the native proximal and distal ends 12, 14 of the bone 10 with the proximal and distal stem components 20, 22 and spacer component 24 must be distracted, or moved in the proximal-distal direction, by at least a distance "d" (shown in FIG. 2), corresponding with the length of the Morse taper post 28 so that the Morse taper post 28 can be inserted into the mating female portion of the spacer component 24. In the illustrated embodiment, the dimension "d" is typically on the order of 20 mm. This degree of proximal-distal distraction of the native bone ends 12, 14 could damage the surrounding soft tissue and soft tissue that is connected to the native bone ends 12, 14.

To avert the potential for soft tissue damage, the present invention obviates the need for proximal-distal distraction of the native bone ends 12, 14. In the present invention, first and second stem members 40, 42, shown in FIGS. 4–5, can be connected to each other without undue distraction of the native proximal and distal end bone portions 12, 14.

Figure 16:
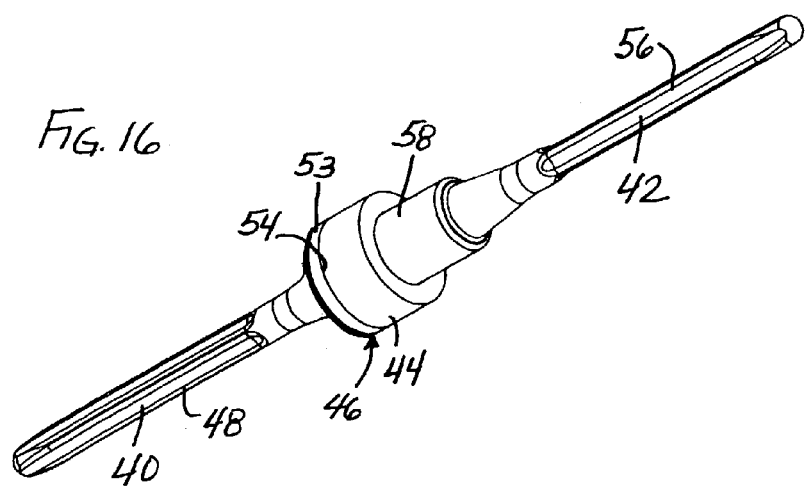
FIG. 16 is a perspective view of the assembled intercalary implant of FIG. 14.
Figure 17:
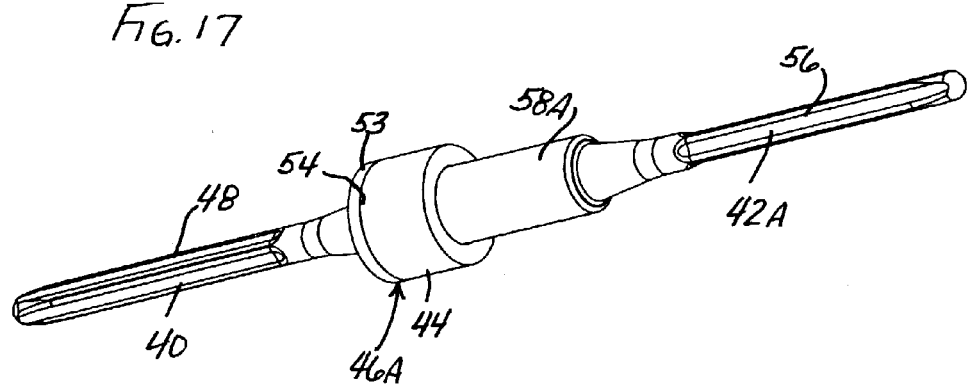
FIG. 17 is a perspective view of the assembled intercalary implant of FIG. 15.
Figure 18:
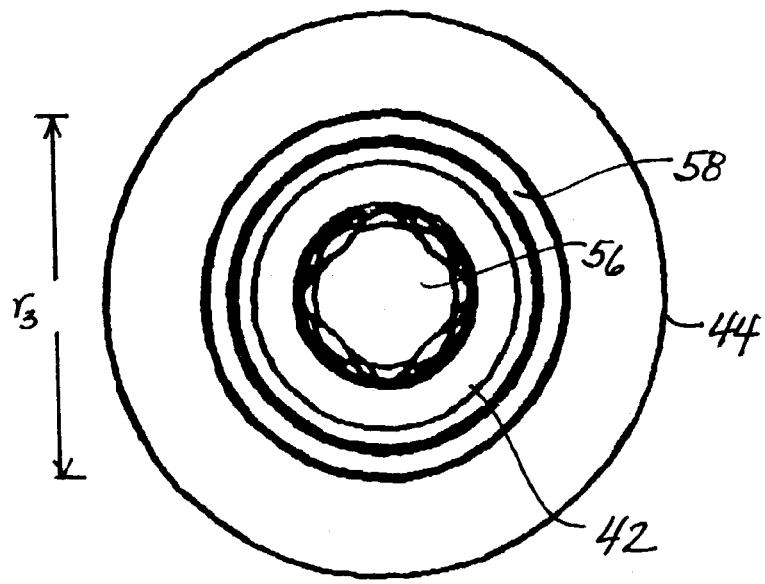
FIG. 18 is an end view of the assembled intercalary implant of FIG. 14, taken from the perspective of line 18—18 of FIG. 14.
Figure 19:
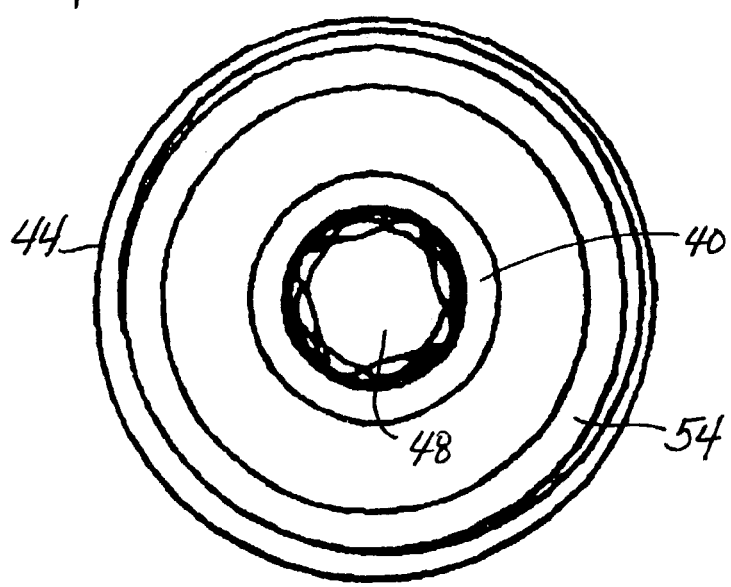
FIG. 19 is an end view of the assembled intercalary implant of FIG. 14, taken from the perspective of line 19—19 of FIG. 14.
Figure 22:
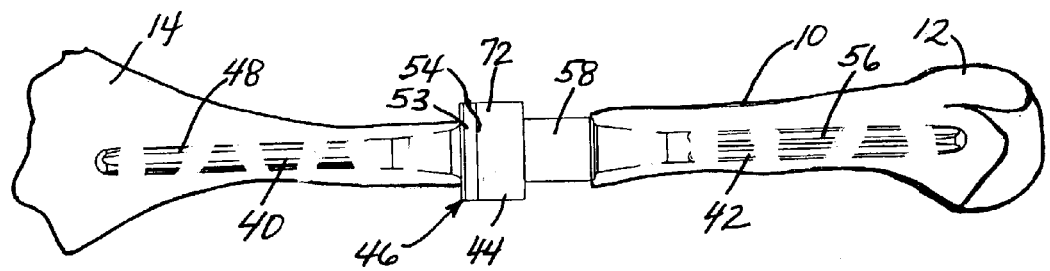
FIG. 22 is a top plan or anterior view of two end portions of a humerus with the assembled intercalary implant of the present invention implanted.

The first and second stem members 40, 42 of the present invention can be connected by means of a collar 44, shown in FIGS. 8–12, to form an assembly that defines the mid-shaft or intercalary implant of the present invention shown at 46 in FIGS. 14, 16 and 22. The mid-shaft or intercalary implant 46 comprises first and second stem members or components. A surgical kit including the intercalary prosthesis 46 of the present invention could include one or more stem members of a different overall axial length, shown at 42A in FIGS. 15 and 17, and as an assembly at 46A in FIGS. 15 and 17. All of the components 40, 42, 44 can be made of standard medical grade material for implants, such as standard titanium alloys and cobalt-chrome alloys.

Figure 20:
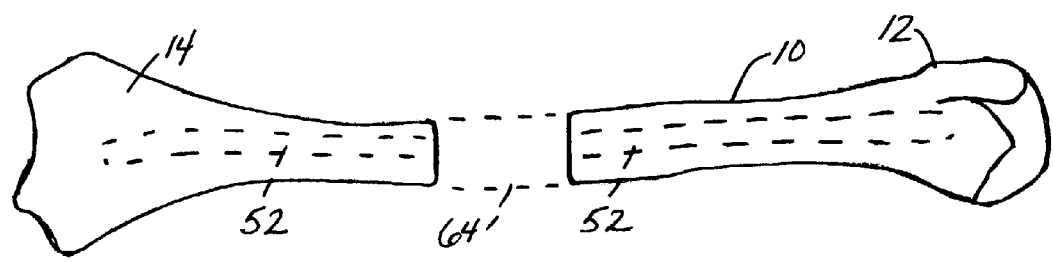
FIG. 20 is a top plan or anterior view of two end portions of a humerus with a gap illustrating where part of the bone shaft has been removed.
Figure 21:
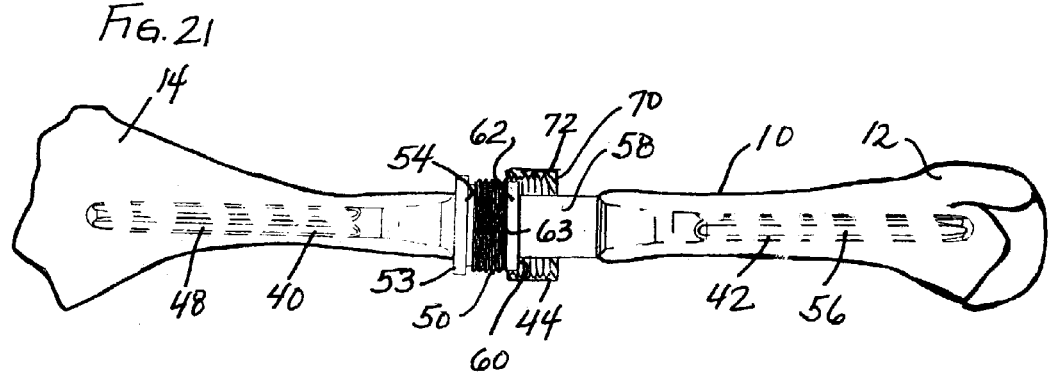
FIG. 21 is a top plan or anterior view of the two end portions of the humerus of FIG. 20 shown with two stem portions of the present invention implanted, prior to the final assembly of the intercalary implant.

As shown in FIG. 4, the first stem member 40 includes a stem portion 48 and a threaded male portion 50. In the illustrated embodiment, the threaded male portion 50 and stem portion 48 are integral, although it should be understood that the invention is not limited to an integral structure unless expressly called for in the claims. The stem portion 48 of the first stem member 40 may have features that allow it to be either cemented or press fit into the intramedullary canal (shown at 52 in FIG. 20) of the end portion of the native bone; for example, part or all of the stem portion can have a porous surface. It should be understood that although FIGS. 21–22 illustrate the first stem member 40 being implanted in a distal end portion 14 of the humerus 10, the first stem member 40 could be implanted in the proximal end portion 12 of the humerus 10 or proximal or distal end portion of another long bone such as the tibia, femur or radius or ulna.

A surgical kit utilizing the principles of the present invention could include several sizes and types of first stem members 40 with threaded male portions 50; for example, such stem members could be provided with stem portions of different lengths, some of which could have porous surfaces. Generally, at least a set of the first stem members 40 of the surgical kit would include threaded male portions 50 having similar characteristics such as size and thread characteristics, so that all of the first stem members 40 of the set would be interchangeable. Additional sets of first stem members with different sizes of male threaded portions could be included to accommodate different diameters of bone.

The first stem member 40 also includes a stop member 53 defining an enlarged diameter shoulder 54 at the junction of the stem portion 48 and the threaded male portion 50. The enlarged diameter shoulder 54 has a radial dimension shown at "$r_1$" in FIG. 6 and an axial dimension shown at "$a_1$" in FIG. 4.

As shown in FIG. 5, the second stem member 42 or component includes a stem portion 56, a spacer portion 58 and a shoulder 60. The end of the second stem member 42 opposite the stem portion 56 comprises a solid cylindrical disc or stop member as shown at 62 in FIG. 7, and having a radial dimension "$r_2$". The annular surface of the stop member 62 adjacent the spacer 58 defines the shoulder 60. In the illustrated embodiment, the stem portion 56, spacer portion 58 and stop member 62 are integral, although it should be understood that the invention is not limited to an integral structure unless expressly called for in the claims. The stem portion 56 of the second stem member 52 may have features that allow it to be either cemented or press fit into the intramedullary canal 52 of the end portion of the native bone; for example, part or all of the stem portion have a porous surface. It should be understood that although FIGS. 21–22 illustrate the second stem member 42 being implanted in a proximal end portion 12 of the humerus 10, the second stem member 42 could be implanted in the distal end portion 14 of the humerus 10 or proximal or distal end portion of another long bone such as the tibia, femur or radius or ulna.

As shown in FIG. 5, the spacer portion 58 of the second stem member 42 is adjacent the stem portion 56, and is between the stem portion 56 and the shoulder 60 of the stop member 62. In the illustrated embodiment, the spacer portion 58 is generally cylindrical in shape, and has a radial dimension shown at "$r_3$" in FIG. 5. The radial dimension $r_3$ of the spacer portion 58 is greater than the greatest thickness of the stem portion 56. The radial dimension $r_3$ of the spacer portion 58 is large enough so that when the stem portion 56 of the second stem member 42 is implanted in the intramedullary canal 52 of the end bone portion 12, the spacer portion 58 is retained outside of the bone, occupying part of the space left by the removed bone shaft, as shown in FIGS. 21–22.

The axial dimension of the spacer portion, shown at "$a_2$" in FIG. 5, is large enough so that, when combined with the axial dimension of the stop member 62 and axial dimension $a_1$ of the male threaded portion 50, the total length is great enough to span the gap (shown at 64 in FIG. 20) left by the removed bone shaft.

A surgical kit utilizing the principles of the present invention could include several sizes and types of stem members with spacer portions 58 and shoulders 60; for example, such stem members could be provided with stem portions 56 of different lengths, some of which could have porous surfaces. As illustrated in FIGS. 14–17, the axial length $a_2$ of the spacer portion 58 could be varied, such as by increasing the length. A surgical kit utilizing the principles of the present invention could include a third, fourth or more stem members similar to the illustrated second stem member 42, but with spacer portions 58 of gradually increasing axial lengths $a_2$ to provide the surgeon with a kit that can be used to span mid-shaft gaps 64 of various lengths. For example, a kit could include multiple stem members like those shown at 42, where the axial length $a_2$ could increase in 5 mm increments. All of these stem members could be made to be used interchangeably with the collar 44 and first stem member 40. It should be understood that the present invention is not limited to provision of such a kit or to any particular incremental increase in axial length unless expressly called for in the claims. A kit including two stem members with different sizes of spacers 58, 58A is illustrated in FIG. 13 at 65.

The radial dimension $r_2$ of the shoulder 60 is greater than the radial dimension $r_3$ of the spacer 58 of the second stem member 42. Although in the illustrated embodiment the shoulder 60 is annular in shape, other shapes may be used so long as the shoulder 60 serves as a stop to limit movement of the movable collar 44.

It should be understood that "radial dimension" as used throughout this specification and claims should not be interpreted as requiring any particular shape of any portion of the first and second stem members or collar; "radial dimension" should be interpreted as including a width of the relevant portion of the stem members.

An example of a suitable collar member 44 is illustrated in FIGS. 8–12. As there shown, the collar 44 includes an annular base portion 70 and a hollow cylindrical portion 72. In the illustrated embodiment, the annular base portion 70 and the cylindrical portion 72 are integral, although it should be understood that the present invention is not limited to such an integral structure unless expressly called for in the claims.

The annular base portion 70 of the collar 44 has an overall radial dimension shown at "$r_4$" in FIG. 11 and a central opening 74 with a reduced radial dimension shown at "$r_5$" in FIGS. 9 and 11. The central opening 74 is large enough so that the collar 44 can be mounted on the second stem member 42 by inserting the free end of the stem portion 56 through the central opening 74 and sliding the collar 44 up along the length of the stem portion 56 and along the length of the spacer 58 until the annular base portion 70 of the collar 44 abuts the shoulder 60. The radial dimension $r_5$ of the central opening 74 is greater than the largest radial dimension $r_3$ of the spacer 58 and greater than the largest radial dimension $r_6$ of the stem portion 56. The radial dimension $r_5$ of the central opening 74 should be less than the radial dimension $r_2$ of the shoulder 60 so that the shoulder 60 can serve as a stop to limit axial movement of the collar 44 in the direction of the first stem member 40.

The hollow cylindrical portion 72 of the collar 44 is threaded to mate with the threaded male portion 50 of the first stem member 40. The cylindrical portion 72 of the collar 44 is open opposite the base 70 to receive the threaded male portion 50 of the first stem member 40. The cylindrical portion 72 of the collar 44 has an interior radial dimension $r_7$ (shown in FIG. 10) and an axial dimension $a_3$ (shown in FIG. 11). The interior radial dimension of the cylindrical portion is greater than the radial dimension of the spacer 58 and greater than the radial dimension of the shoulder 60.

In the illustrated embodiment, the mating threaded parts, that is, the male threaded portion 50 of the first stem member 40 and the collar 44, have a locking threaded relationship. One way of producing such a locking threaded relationship is to form a wedge ramp in the threads of the female collar 44 using equipment available from Spiralock Corporation, a Detroit Tool Industries Company, of Madison Heights, Mich. A locking threaded relationship is valuable in limiting possible loosening of the threaded connection through vibration or use. It should be understood that use of a wedge ramp and use of Spiralock Corporation equipment are identified as examples only; the present invention is not limited to the use of locking threads or any particular types of locking threads unless expressly called for in the claims.

The collar 44 has an extended position and a retracted position on the second stem member 42. In the extended position shown in FIGS. 14–17 and 22, the annular base portion 70 of the collar 44 is spaced from the stem portion 56 of the second stem member 42 and abuts the shoulder 60 of the second stem member 42. In this extended position, the cylindrical portion 72 of the collar 44 extends over and beyond the shoulder 60 and stop member 62 of the second stem member 42. The extended position of the collar 44 is at the end of its possible range of motion along the second stem member 42. The collar 44 is movable along the stem member 42 away from the extended position to several possible retracted positions. In at least one of the retracted positions, shown in FIG. 13, at least the shoulder 60 of the second stem member 42 is exposed beyond the collar 44. Another retracted position is illustrated in FIG. 21; as shown in FIG. 21, the end surface of the stop member 62 that defines the shoulder 60 is exposed.

The present invention also provides a method of replacing a missing part of the shaft of a long bone, such as part 64 of bone 10. The long bone 10 is prepared so that proximal and distal portions 12, 14 of the long bone remain. The distal end of the proximal portion 12 and proximal end of the distal portion 14 can be resected in a standard manner and cut or planed to define flat planar surfaces. The intramedullary canals 52 of the proximal and distal portions 12, 14 of the long bone 10 can be reamed in a standard manner to prepare the bone portions 12, 14 to receive the implant 46.

Suitable trials duplicating the span that will be provided by the intercalary implant 46 can be used prior to implantation to ensure that the length of the intercalary implant 46 will be appropriate.

One of the stem portions of one of the stem members is implanted in the intramedullary canal of the proximal portion of the bone and the stem portion of the other stem member is implanted in the intramedullary canal of the distal portion of the bone. In the embodiment illustrated in FIGS. 21–22, the first stem member 40 is implanted in the distal end portion 14 of the bone 10 and the second stem member 42 is implanted in the proximal end portion 12 of the bone 10. It should be understood that the first stem member 40 could be affixed to either the proximal portion 12 or the distal portion 14 of the bone 10, and the second stem member 42 could be affixed to either the proximal portion 12 or distal portion 14 of the bone 10.

It should be understood that the present invention could involve use of stem members 40, 42 with stem portions 56 designed to be cemented in place in the intramedullary canal or stem members with stem portions designed to be interference fit in the intramedullary canal. The surgical method used will include appropriate steps to accommodate the design selected for the particular patient.

When implanted, the shoulder 54, stop member 53 and male threaded portion 50 of the first stem member 40 are exposed beyond the end surface of the bone end; the remainder of the first stem member 40 is received in the bone end. When implanted, the spacer 58 and disc or stop member 62 of the second stem member 42 are exposed beyond the end surface of the bone end. The entire collar 44 is also exposed outside of the bone.

After the two stem portions 40, 42 have been implanted, assembly of the intercalary implant 46 may then be completed. As shown in FIG. 21, the outer edge of the male threaded portion 50 of the first stem member 40 is positioned against the outer surface of the stop member 62 of the second stem member 42. The two stem members 40, 42 can be so positioned without distracting the proximal and distal portions 12, 14 of the bone in the proximal-distal direction. The collar 44 is then moved axially along the spacer 58 and threaded onto the male portion 50 of the first stem member 40; the collar 44 is tightened on the threaded male portion 50 of the first stem member 40 until the base 70 of the collar abuts the shoulder 60 of the second stem member 42 and the outer edge of the collar 44 abuts the outer surface of the shoulder 54 of the stop member 53 of the first stem member

40. The two stem members 40, 42 and the collar 44 are thereby securely assembled together without any distraction of the proximal and distal portions 12, 14 of the bone 10 in the proximal-distal direction. Thus, potential damage to the soft tissue at the ends of the bone 10 is eliminated or at least substantially reduced.

An assembly of the components 40, 42, 44 of the intercalary implant is illustrated in FIG. 22 with respect to the humerus, and shown without being implanted in FIGS. 14–17. When assembled, the free end of the male portion 50 of the first stem member 40 abuts the outer surface 63 of the stop member 62 of the second stem member 42. The opposite shoulder 60 of the stop member 62 of the second stem member 42 abuts the inner surface of the annular base 70 of the collar 44. The threaded cylindrical portion 72 of the collar 44 extends over and engages the threaded male portion 50 of the first stem member 40. The outer edge of the threaded cylindrical portion 72 abuts the shoulder 54 of the stop member 53 of the first stem member 40. Thus, when assembled, the overall length of the intercalary implant 46 is fixed, and the overall length of the part of the intercalary implant spanning the gap left in the bone shaft is fixed as the total of the axial dimensions of the spacer 58 of the second stem member 42, collar 44 and stop member 53 of the first stem member 40.

It should be understood that the overall length of the part of the intercalary implant spanning the gap left in the bone shaft could also include a part of the male threaded portion 50 of the first stem member 40 if for some reason the collar 44 is not tightened until it abuts the shoulder 54 of the first stem member 40.

It should be understood that the above-described surgical technique is provided by way of example only, and that the present invention is not limited to that technique unless expressly called for in the claims.

An alternative intercalary prosthesis, kit and method is disclosed in an application for U.S. Patent filed concurrently herewith by Stephen A. Hazebrouck and entitled "Intercalary Prosthesis, Kit and Method," which is incorporated by reference herein in its entirety.

While only specific embodiments of the invention have been described and shown, it is apparent that various alternatives and modifications can be made thereto. Those skilled in the art will also recognize that certain additions can be made to the illustrative embodiments. For example, a spacer element could also or alternatively be provided on the first stem member 40 between the threaded male portion 50 and the stem portion 48. It is, therefore, the intention in the appended claims to cover all such alternatives, modifications and additions as may fall within the true scope of the invention.

We claim:

1. An intercalary implant for use in replacing a missing portion of the shaft of a long bone, wherein the long bone includes native proximal and distal portions having intramedullary canals, the implant comprising:

a first stem member including a stem portion to be received in the intramedullary canal of one of the native portions of the long bone, the first stem member including a threaded male portion to be positioned outside of the intramedullary canal;

a second stem member including a stem portion to be received in the intramedullary canal of the other of the native portions of the long bone, the second stem member further including a spacer portion to be positioned outside of the intramedullary canal and a shoulder to be positioned outside of the intramedullary canal, the spacer portion being between the stem portion and the shoulder; and a collar including an annular base portion with an opening and a cylindrical portion open at one end, the cylindrical portion having a threaded interior surface to receive and mate with the threaded male portion of the first stem member;

wherein the collar receives part of the second stem member through the opening in the base portion of the collar, and the collar is movable in a proximal-distal direction along at least part of the length of the spacer portion of the second stem member between an extended position and a retracted position;

wherein in the extended position the annular base portion of the collar is spaced from the stem portion of the second stem member and abuts the shoulder of the second stem member and the cylindrical portion of the collar extends over and beyond the shoulder of the second stem member;

wherein in the retracted position the collar is positioned so that at least part of the shoulder is exposed; and wherein the shoulder and the opening of the annular base portion of the collar are sized and shaped so that when the collar is threaded onto the threaded male portion of the first stem member the position of the first stem member is fixed with respect to the position of the second stem member.

2. The intercalary implant of claim 1 wherein:

the shoulder of the second stem member has a radial dimension and an axial dimension;

the opening in the annular base portion of the collar has a radial dimension;

the spacer of the second stem member has a radial dimension and an axial dimension;

the cylindrical portion of the collar has an interior radial dimension and an axial dimension;

the radial dimension of the shoulder of the second stem member is greater than the radial dimension of the opening in the annular base portion of the collar;

the interior radial dimension of the cylindrical portion of the collar is greater than the radial dimension of the spacer of the second stem member;

the interior radial dimension of the cylindrical portion of the collar is greater than the radial dimension of the shoulder of the second stem member; and the axial dimension of the cylindrical portion of the collar is greater than the axial dimension of the shoulder of the second stem member.

3. The intercalary implant of claim 1 wherein the stem portion and threaded male portion of the first stem member are integral.

4. The intercalary implant of claim 1 wherein the shoulder, spacer and stem portion of the second stem member are integral.

5. A surgical kit for use in treating a long bone of a patient wherein a portion of the shaft of the long bone is missing or resected and native proximal and distal portions of the long bone remain, the kit comprising:

a first stem member including a stem portion and a threaded male portion;

a second stem member having an overall axial dimension and including a stem portion, a spacer portion having an axial dimension and a radial dimension, and a shoulder having an axial dimension and a radial dimension, the spacer portion being between the stem portion and the shoulder, the radial dimension of the shoulder being greater than the radial dimension of the spacer portion; and a collar member including an annular base portion with an opening and a cylindrical portion open at one end, the cylindrical portion having a threaded interior surface to receive and mate with the threaded male portion of the first stem member, the cylindrical portion having an interior radial dimension and an axial dimension, the annular base portion having a radial dimension and the opening of the annular base portion having a radial dimension;

wherein the radial dimension of the shoulder of the second stem member is greater than the radial dimension of the opening in the annular base portion of the collar;

wherein the interior radial dimension of the cylindrical portion of the collar is greater than the radial dimension of the spacer of the second stem member and greater than the radial dimension of the shoulder of the second stem member;

wherein the axial dimension of the cylindrical portion of the collar is greater than the axial dimension of the shoulder of the second stem member.

6. The surgical kit of claim 5 further comprising a third stem member having an overall axial dimension and including a stem portion, a spacer portion having an axial dimension and a radial dimension, and a shoulder having an axial dimension and a radial dimension, the spacer portion being between the stem portion and the shoulder, the radial dimension of the shoulder being greater than the radial dimension of the spacer portion;

wherein the overall axial dimension of the third stem member is greater than the overall axial dimension of the second stem member;

wherein the radial dimension of the shoulder of the third stem member is greater than the radial dimension of the opening in the annular base portion of the collar;

wherein the interior radial dimension of the cylindrical portion of the collar is greater than the radial dimension of the spacer of the third stem member and the radial dimension of the shoulder of the third stem member;

wherein the axial dimension of the cylindrical portion of the collar is greater than the axial dimension of the shoulder of the third stem member.

7. The surgical kit of claim 5 wherein the stem portion and the threaded male portion of the first stem member are integral.

8. The surgical kit of claim 5 wherein the stem portion, spacer and shoulder of the second stem member are integral.

9. The surgical kit of claim 6 wherein the stem portion, spacer and shoulder of the third stem member are integral.

10. A method of surgically replacing a missing part of the shaft of a long bone comprising:

preparing the long bone so that proximal and distal portions of the long bone remain, the proximal and distal portions of the long bone each having an intramedullary canal;

providing a first stem member, a second stem member and a collar, wherein the first stem member includes a stem portion and a male threaded portion, the second stem member includes a stem portion, a spacer and a shoulder, and the collar includes a female threaded portion;

implanting the stem portion of one of the stem members in the intramedullary canal of the proximal portion of the long bone;

implanting the stem portion of the other of the stem members in the intramedullary canal of the distal portion of the long bone;

positioning the male portion of the first stem member against the shoulder of the second stem member without distracting the proximal and distal parts of the bone in the proximal-distal direction; and assembling the first stem member, second stem member and collar by threading the collar onto the threaded male portion of the second stem member without distracting the proximal and distal parts of the bone in the proximal-distal direction without inserting any portion of the first stem member into any portion of the second stem member and without inserting any portion of the second stem member into any portion of the first stem member.

11. The surgical method of claim 10 wherein the spacer, shoulder, collar and threaded male portion are positioned between the proximal and distal parts of the bone after the first and second stem members have been implanted and after the first stem member, second stem member and collar are assembled.

12. The surgical method of claim 10 wherein the step of assembling the first stem member, second stem member and collar comprises moving the collar along the spacer until the collar abuts the shoulder of the second stem member.

13. An intercalary implant usable in combination with, a proximal portion of a long bone, the proximal portion having an intramedullary canal and a resected end surface, a distal portion of the long bone, the distal portion having an intramedullary canal and a resected end surface, the two resected end surfaces being spaced from each other, the intercalary implant comprising:

a first stem member having a stem portion received in the intramedullary canal of one of the portions of the long bone;

a second stem member having a stem portion received in the intramedullary canal of the other portion of the long bone;

a male threaded member connected to the stem portion of one stem member, the male threaded member having an end opposite the connection to the stem portion;

a collar having a female threaded portion; and a spacer connected to the stem portion of the other stem member;

a stop member and a shoulder at the end of the spacer opposite the connection between the spacer and the stem member, the stop member and shoulder being connected to the spacer;

wherein the male threaded member abuts the stop member in an end-to-end relationship;

wherein at least a portion of the collar bears against a portion of the shoulder and at least a portion of the collar extends over the stop member and threadedly engages the male threaded member;

wherein the distance between the resected end surfaces of the bone portions is fixed by the intercalary implant.

14. The combination of claim 13 wherein the bone portions and intercalary implant are in tension.

15. The combination of claim 13 wherein the male threaded member and stem portion of the first stem member are integral.

16. The combination of claim 13 wherein the spacer, stop member, shoulder and stem portion of the second stem member are integral.

* * * * *